United States Patent [19]

Müller

[11] Patent Number: 4,902,393

[45] Date of Patent: Feb. 20, 1990

[54] PROCESS FOR THE PRODUCTION OF 1,1,2-TRICHLORO-2-METHYLPROPANE

[75] Inventor: Dieter J. Müller, Marl, Fed. Rep. of Germany

[73] Assignee: Huels Aktiengesellschaft, Marl, Fed. Rep. of Germany

[21] Appl. No.: 644,466

[22] Filed: Aug. 27, 1984

[30] Foreign Application Priority Data

Aug. 25, 1983 [DE] Fed. Rep. of Germany ....... 3330609
Apr. 25, 1984 [DE] Fed. Rep. of Germany ....... 3415334

[51] Int. Cl.$^4$ ................... C07G 13/00; C07C 17/04
[52] U.S. Cl. ........................... 204/158.12; 570/261
[58] Field of Search ................ 204/163 R, 158.12; 570/246, 247, 251, 253, 255, 261

[56] References Cited

U.S. PATENT DOCUMENTS

| | | | |
|---|---|---|---|
| 1,741,305 | 12/1929 | Jaeger | 204/163 R |
| 2,302,228 | 11/1943 | Kharasch et al. | 570/261 |
| 2,764,619 | 9/1956 | Ikenberry et al. | 570/261 |
| 3,137,644 | 6/1964 | Bretschneider | 204/163 R |
| 3,405,046 | 10/1968 | Sennewald et al. | 204/163 R |

*Primary Examiner*—J. E. Evans
*Attorney, Agent, or Firm*—Millen, White & Zelano

[57] ABSTRACT

A process for the production of 1,1,2-trichloro-2-methylpropane comprises reacting 1-chloro-2-methylpropene with sulfuryl chloride. This reaction takes place preferably under the effect of light, especially UV light and/or in the presence of an aldehyde as the catalyst. The starting material contains less than 10 ppm of N-containing compounds conventionally employed to stabilize it.

18 Claims, No Drawings

PROCESS FOR THE PRODUCTION OF 1,1,2-TRICHLORO-2-METHYLPROPANE

BACKGROUND OF THE INVENTION

The present invention relates to a process for the production of 1,1,2-trichloro-2-methylpropane by the reaction of 1-chloro-2-methylpropene with sulfuryl chloride, preferably in the presence of light, especially UV light and/or in the presence of an aldehyde as the catalyst.

No process has been known heretofore permitting the production of 1,1,2-trichloro-2-methylpropane selectively from C4-compounds. This compound can be used for several purposes, e.g. as a starting material for the preparation of pharmaceuticals and of insecticides as well as an intermediate for other C4-derivatives, this compound is expected to become more interesting for organic reactions, since it is now readily available for the first time.

In the prior art, this compound has been obtained as a by-product from various reactions. For example, this compound is obtained in minor quantities in the direct chlorination of isobutene, as a higher-chlorinated by-product which is difficult to isolate. The primary products are 3-chloro-2-methylpropene and 1-chloro-2-methylpropene. Also produced are other tri-, tetra-, and pentachloro derivatives.

Photochemical chlorination of isobutene in the gaseous phase also yields 1,1,2-trichloro-2-methylpropane merely as a by-product [Beilstein E III 1, p. 320 (1958) : Ing. eng. Chem. 40 (1948) : 1488].

Further chlorination of already partially chlorinated C4-compounds likewise takes place with little selectivity. Thus, the chlorination of 2-chloro- and 1,2-dichloro-2-methylpropane in the liquid phase yields 1,1,2-trichloro-2-methylpropane only as a by-product [Beilstein E III 1, p. 320 (1958) : Am. Soc. 58 (1936) : 1028, 1029], even if the process is conducted in the presence of AlCl3 [Beilstein E IV 1, p. 293 (1972) : Bl. Chem. Soc. Japan 30 (1957) : 218, 220].

Chlorination of 1-chloro-2-methylpropene in the presence of sodium bicarbonate at 0° C. yields, besides 68% 3,3-dichloro-2-methylpropene, only 32%, 1,1,2-trichloro-2-methylpropane [Chem. Abstr. 33 (1939) : 4190].

All of these conventional processes have the common disadvantage that the desired 1,1,2-trichloro-3-methylpropane is obtained only as a by-product.

SUMMARY OF THE INVENTION

Accordingly, it is an object of this invention to provide a process permitting production of 1,1,2-trichloro-2-methylpropane as the main product in a technically simple way.

Upon further study of the specification and appended claims, further objects and advantages of this invention will become apparent to those skilled in the art.

These objects have been attained according to this invention by reacting 1-chloro-2-methylpropene with sulfuryl chloride, preferably under the effect of light, especially UV light and/or in the presence of an aldehyde as the catalyst according to the formula set out below, preferably in the liquid phase at a temperature of 30° to 65° C.

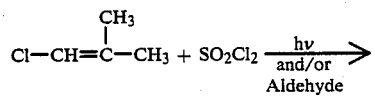

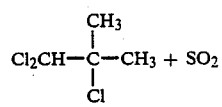

DETAILED DISCUSSION

Reaction of sulfuryl chloride with the isomeric 3-chloro-2-methylpropene yields, in a conventional addition reaction, 1,2,3-trichloro-2-methylpropane with a satisfactory yield of 83% [J. Am. Chem. Soc. 68 (1946) : 787].

Surprisingly, the analogous reaction of sulfuryl chloride with 1-chloro-2-methylpropene does not lead to a clear result. The reaction, which can be observed by the release of gaseous SO2, proceeds very slowly, on the one hand; on the other hand, the spectrum of products is hard to reproduce. Besides the desired 1,1,2-trichloro-2-methylpropane, varying amounts of 3,3-dichloro-2-methylpropene and 1,3-dichloro-2-methylpropene, in particular, are likewise formed.

It has been found that the unsatisfactory reproducibility of the array of products can be attributed to the presence of small traces of various stabilizers in the ppm range in 1-chloro-2-methylpropene. It has been discovered, in this regard, that several customary stabilizers for chlorinated hydrocarbons affect the reaction with respect to velocity, as well as the array of products, and exhibit a catalyzing or inhibiting effect. For stabilizer blends, the effects can compensate one another, or can be magnified. In particular, the presence of nitrogen-containing bases is disadvantageous because these shift the course of the reaction in the direction toward substitution. Preferred for the reaction of this invention is a 1-chloro-2- methylpropene containing less than 1 ppm preferably less than 10 ppm of a stabilizer, if the stabilizer is a nitrogen containing base. Typical nitrogen containing stabilizers are diisopropylamine, triethylamine, N-methylmorpholine, N-methylpyrrole, diaziridine, pyrazine, N-methylhydroxylamine, benzotriazole.

When light energy is used in the process, the amount of stabilizer tolerable is up to 10ppm, and when an aldehyde is used in the process, the amount of stabilizer tolerable is also up to 10 ppm. Optionally, the starting material can be purified to meet these levels.

With the use of such a substantially stabilizer-free 1-chloro-2-methylpropene, it has been found that the reaction with sulfuryl chloride, though yielding predominantly 1,1,2-trichloro-2-mehtylpropane, proceeds at a relatively slow rate. In a further development of the process, it has been discovered, surprisingly, that the presence of light, particularly UV light, accelerates the reaction and furthermore also shifts the reaction practically quantitatively in the direction toward the addition product. Radiation of a wavelength of 200–400 nm is especially suitable as the actinic radiation. Intensities are not critical and sources are not critical. Typically, radiation intensities of 15W - 10 kW or even more can be used, e.g., from conventional mercury lamps, e.g., Original Hanau Heraeus Lamps. Under the influence of radiation, typical reaction temperatures are 30°–65° C., reaction times 60–240 min and reaction pressures 0.5–3 bar, preferably normal pressure. Using light, yields are usually 90–98 mole %.

Instead of using light, the reaction can also be conducted in the presence of an aldehyde as the catalyst, preferably an aliphatic or olefinic aldehyde. Typically, suitable aldehydes will be those of $C_{2-10}$-alkyl groups or $C_{3-10}$-alkenyl groups. Isobutanal is an example. This aldehyde has the advantage of not being foreign to the system since it often initially will be present in trace amounts in the 1-chloro-2-methylpropene starting material as a result of preceding hydrolytic and/or oxidative processes. Other suitable aldehydes are acrolein, crotonaldehyde, propionaldehyde, glycolaldehyde, benzeldehyde etc.

It has been found that concentrations as low as 10–100 ppm of the aldehydes are catalytically active and enhance the reaction in the direction toward addition, i.e., increase the yield of desired product. The reaction rate, though, is lower than when the reaction is carried out in the presence of UV light.

In general, concentrations of 10–10,000 ppm of an aldehyde are employed; preferably, about 100 ppm to 1,000 ppm of an aldehyde is added, although higher concentrations of up to 10,000 ppm and more will be suitable. Selectivities of up to 96% can thereby be attained for the reaction of 1-chloro-2-methylpropene to yield 1,1,2-trichloro-2-methylpropane. When an aldehyde is used, typical reaction temperatures are 30°–65° C., reaction times are 90–360 minutes and reaction pressures are 0.5–3 bar, preverably normal pressure. Using an aldehyde, yields are usually 90–96 mole %.

The reaction can also be carried out both in the presence of light and in the presence of an aldehyde as the catalyst.

It has thus become possible for the first time to produce 1,1,2-trichloro-2-methylpropane from 1-chloro-2-methylpropene with a selectivity above 99%. The method is suited for discontinuous mode, for example in an agitator-equipped reactor, and for continuous mode, for instance in a tubular reactor or in a cascade.

Preferably, the reaction is conducted in the liquid phase. The sulfuryl chloride can be used in a stoichiometric quantity, based on 1-chloro-2-methylpropene. A quantity less than stoichiometric (e.g., 65–95 % of the stoichiometric amount) is preferably employed because unreacted, excess 1-chloro-2- methylpropene can be more easily separated than excess sulfuryl chloride. However, an excess of sulfuryl chloride is not deleterious to the reaction per se. It is also possible to conduct the reaction in solvents such as $CCl_4$ or other inert diluents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A stirred apparatus with reflux condenser and dropping funnel, with a mercury high-pressure immersion lamp having been introduced into the apparatus, is charged with 87 g of stabilizer-free 1-chloro-2-methylpropene (stabilizer content below 1 ppm), heated to 45° C., and within 2 minutes 108 g of $SO_2Cl_2$ is added in metered amounts while controlling the temperature of the agitated flask by means of a thermostat.

The experiment is conducted once without and once with the effect of light, otherwise in the same way. The gaseous $SO_2$ and in some cases a certain amount of HCl, released during the reaction, are withdrawn via the cooler. The reaction is terminated once evolution of $SO_2$ has ceased.

Thereafter, the crude produce is washed with water, dried over $K_2CO_3$, and subjected to analysis by gas chromatography to determine the composition of the product.

The results of the experiments are shown in Table 1.

TABLE 1

Reaction of Stabilizer-Free 1-Chloro-2-methylpropene with Sulfuryl Chloride with and without Effect of UV Light

| UV Light | Reaction Temperature °C. | Reaction Period min | Amount of crude Product g | Composition of Pure Product, % (*) | | |
|---|---|---|---|---|---|---|
| | | | | 3,3-Dichloro-2-methylpropene | 1,3-Dichloro-2-methylpropene | 1,1,2-Trichloro-2-methylpropane |
| Without | 45–50 | 300 | 138 | 12.5 | 1.5 | 82.0 |
| With | 45–50 | 150 | 145 | 0.2 | 0.5 | 99.0 |

(*) Remainder up to 100% not identified in detail. calculated free of 1-Chloro-2-methylpropene

EXAMPLE 2

An agitator-equipped apparatus with reflux condenser and dropping funnel is charged with 90.6 g of 1-chloro-2-methylpropene, free of nitrogen-containing stabilizers, heated to 45° C., 100 ppm of isobutyraldehyde or 1,000 ppm of acrolein, respectively, is added thereto, and within 60 minutes, 108 g of $SO_2Cl_2$ is added in metered amounts while controlling the temperature of the agitated flask by means of a thermostat.

The $SO_2$ liberated during the reaction and removed in gaseous form and, in some cases, a certain amount of HCl, are withdrawn via the cooler. The reaction is terminated once evolution of $SO_2$ has ceased.

The crude product is then washed with water, deacidified and dried over $K_2CO_3$, and subjected to analysis by gas chromatography to determine the product composition.

Table 2 shows the results of the experiments.

TABLE 2

Reaction of Stabilizer-Free 1-Chloro-2-methylpropene with Sulfuryl Chloride in the Presence of Aldehydes

| Aldehyde ppm | Reaction Temp. °C. | Reaction Period Incl. Feeding Time of $SO_2Cl_2$ | | Amount of Crude Product g | Composition of Pure Product, % (*) | | |
|---|---|---|---|---|---|---|---|
| | | Total Time min | Feeding Time min | | 3,3-Dichloro-2-methylpropene | 1,3-Dichloro-2-methylpropene | 1,1,2-Trichloro-2-methylpropane |
| Isobutanal 100 | 45–50 | 240 | 60 | 144 | 1.5 | 1.0 | 96.0 |
| Acrolein 1,000 | 45–50 | 240 | 60 | 142 | 2.5 | 1.5 | 94.0 |

(*) Remainder up to 100% not identified in detail. calculated free of 1-Chlor-2-methylpropene The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the production of 1,1,2-trichloro-2-methylpropane, comprising reacting 1-chloro-2-methylpropene with sulfuryl chloride wherein the 1-chloro-2-methylpropene contains less than about 10 ppm of a stabilizer therefor which stabilizer in greater amounts would interfere with said reaction whereby 1,1,2-trichloro-2-methylpropane is produced essentially selectively and in high yield.

2. A process of claim 1, wherein said stabilizer is a nitrogen containing base.

3. A process of claim 1, wherein the reaction is carried out in the presence of actinic radiation.

4. A process of claim 3, wherein the reaction is carried out in the presence of U.V. light.

5. A process of claim 4, wherein the reaction is carried out in the presence of light having a wavelength of about 200–400 nm.

6. A process of claim 1, wherein the reaction is carried out in the presence of an aldehyde effective to increase the yield of 1,1,2-trichloro-2-methylpropane.

7. A process of claim 6, wherein the aldehyde is based on a $C_{2-10}$-alkane or a $C_{3-10}$-alkene.

8. A process of claim 7, wherein the aldehyde is isobutanal or acrolein.

9. A process of claim 6, wherein the aldehyde is present in a concentration of about 10–10,000 ppm.

10. A process of claim 9, wherein the aldehyde is present in a concentration of about 100–1,000 ppm.

11. A process of claim 6, wherein the reaction is carried out in the presence of actinic radiation.

12. A process of claim 1, wherein the reaction is carried out in the liquid phase.

13. A process of claim 1, wherein the reaction is carried out at a temperature of about 30°–65° C. under ambient pressure.

14. A process of claim 1, wherein the sulfuryl chloride is present in less than the stoichiometric quantity, based on 1-chloro-2-methylpropene.

15. A process of claim 1 further comprising, prior to said reaction, purifying 1-chloro-2-methylpropene starting material containing more than about 10 ppm of said stabilizer so that it contains less than about 10 ppm of said stabilizer.

16. A process of claim 4 wherein said 1,1,2-trichloro-2-methylpropane is produced with a yield of at least 90%.

17. A process of claim 6 wherein said 1,1,2-trichloro-2-methylpropane is produced with a yield of at least 90%.

18. A process of claim 3 further comprising, prior to said reaction, purifying 1-chloro-2-methylpropene starting material containing more than about 10 ppm of said stabilizer so that it contains less than about 10 ppm of said stabilizer.

* * * * *